United States Patent

Naya

[11] Patent Number: 6,043,485
[45] Date of Patent: Mar. 28, 2000

[54] SAMPLE ANALYZER

[75] Inventor: Masayuki Naya, Kanagawa-ken, Japan

[73] Assignee: Fuji Photo Film Co., Ltd., Kanagawa-ken, Japan

[21] Appl. No.: 09/182,210

[22] Filed: Oct. 30, 1998

[30] Foreign Application Priority Data

| Oct. 30, 1997 | [JP] | Japan | 9-298708 |
| Oct. 30, 1997 | [JP] | Japan | 9-298709 |

[51] Int. Cl.$^7$ ................................ H01J 3/14
[52] U.S. Cl. .................... 250/234; 250/216; 250/306
[58] Field of Search ........................ 356/375, 376; 250/234, 306, 216, 307, 227.26, 227.11, 236, 227.28; 385/12, 123, 133; 359/368, 385, 389, 894

[56] References Cited

U.S. PATENT DOCUMENTS

| 5,288,998 | 2/1994 | Betzig et al. | 250/227.26 |
| 5,693,938 | 12/1997 | Marchman et al. | 250/306 |
| 5,789,742 | 8/1998 | Wolff | 250/234 |
| 5,838,000 | 11/1998 | Mertesdorf et al. | 250/306 |

*Primary Examiner*—Hoa Q. Pham
*Attorney, Agent, or Firm*—Sughrue, Mion, Zinn Macpeak & Seas, PLLC

[57] ABSTRACT

A sample analyzer includes a light source for emitting light for analyzing a sample and a probe having at its one end a light outlet aperture which is smaller in diameter than the wavelength of the light emitted from the light source. An incident optical system causes the light emitted from the light source to enter the probe through the other end of the probe. A sample support supports the sample in a position where the sample is exposed to near field light emitted from the light outlet aperture of the probe. A diffusion panel receives scattered light generated by interaction between the surface of the sample and the near field light and visualizes the intensity distribution pattern of the scattered light. A CCD image taking device takes an image of the intensity distribution pattern of the scattered light visualized by the diffusion panel, and the image of the intensity distribution pattern of the scattered light taken by the image taking device is displayed on a CRT.

4 Claims, 3 Drawing Sheets

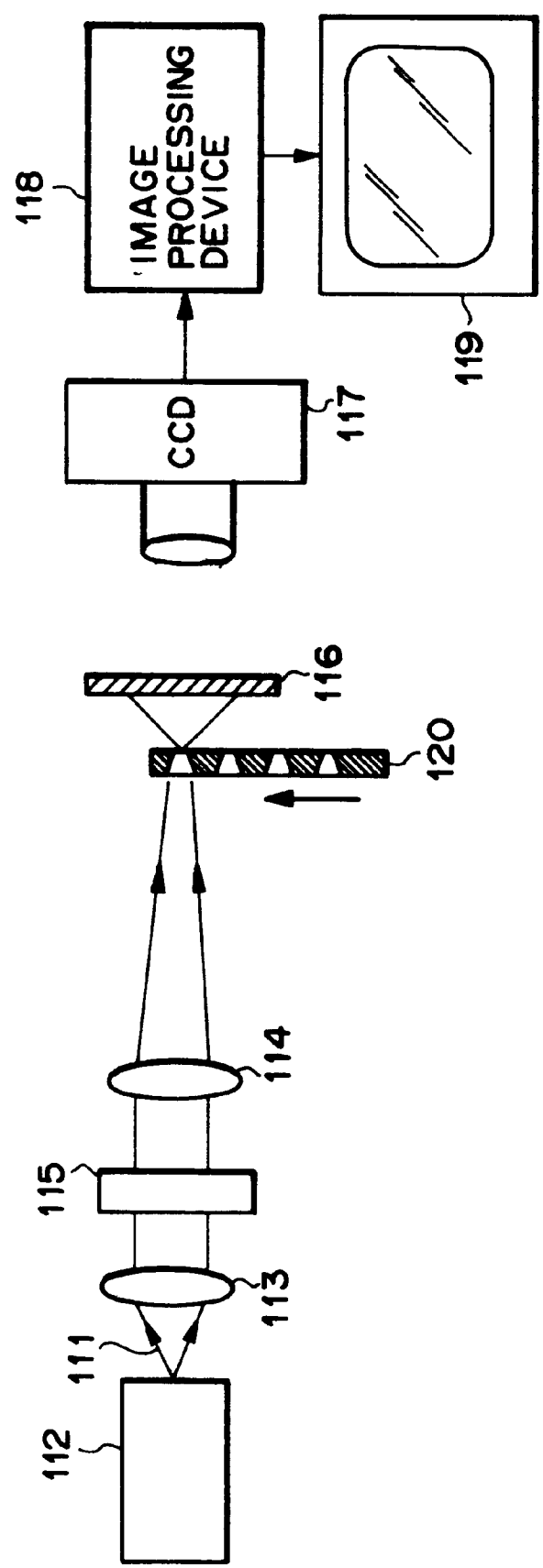

SAMPLE ANALYZER

BACKGROUND OF THE INVENTION

1. Field of the Invention

This invention relates to a sample analyzer for analyzing a sample by use of near field light emitted from a nano-aperture of a probe.

2. Description of the Related Art

There has been known a near field optical microscope such as a scanning photon type tunnel microscope as a system which can analyze the shape and/or structure of sample which is smaller than a wavelength of light. In the near field optical microscope, near field light (evanescent light) is projected onto the surface of a sample through a nano-aperture of a probe and the intensity of scattered light generated by interaction between the surface of the sample and the near field light, that is, disturbance of the near field (evanescent field) by the surface of the sample is detected, and information on the shape and/or structure of the surface of the sample is obtained by causing the probe to scan the surface of the sample and taking a scattered light intensity detecting signal in time series as a function of the position of the probe.

The probe with a nano-aperture is generally prepared by sharpening an end of an optical fiber by etching, depositing metal film on the sharpened end and removing a part of the metal film.

Even with the near field optical microscope, information on more detail of the sample such as orientation of molecules at each part of the surface of the sample cannot be obtained.

Further in the probe with a nano-aperture, propagation loss of light varies according to the shape of the nano-aperture, and the intensity distribution pattern of the near field light, which is an evanescent wave, varies according to the shape of the nano-aperture, which affects the result of the analysis. Accordingly, the shape of the nano-aperture of the probe must be evaluated in order to check the performance of the probe.

This check has been conventionally carried out by observation through an electron microscope. However this method is a destructive inspection and cannot be used for checking a probe to be actually used.

Further since the intensity distribution pattern of the evanescent light is also related to the state of polarization of the light which enters the probe, it is required when a probe is used to determine in advance the correlation between the intensity distribution pattern of the evanescent light and the state of polarization of the light which enters the probe and to select an optimal state of polarization. For this purpose, the intensity distribution pattern of the near field light must be actually detected and conventionally the intensity distribution pattern of the near field light through a probe to be checked is detected by scanning of another probe.

However this method is disadvantageous in that it requires skill, takes a long time and is low in yield. Further since the probe for measurement affects the intensity distribution pattern of the near field light emanating from the probe to be checked, reliability of evaluation is low.

In various instruments using the near field light other than the near field optical microscope, devices with a nano-aperture are employed and evaluation of the nano-aperture is required.

SUMMARY OF THE INVENTION

In view of the foregoing observations and description, the primary object of the present invention is to provide an analyzer which can analyze the structure of a sample in more detail.

Another object of the present invention is to provide a nano-aperture evaluation system which can accurately and easily evaluate the intensity distribution pattern of near field light emitted from a nano-aperture, an optical state of polarization of light to be caused to enter the probe, and the like.

In accordance with a first aspect of the present invention, there is provided a sample analyzer comprising a light source for emitting light for analyzing the sample, a probe having at its one end a light outlet aperture which is smaller in diameter than the wavelength of the light emitted from the light source, an incident optical system which causes the light emitted from the light source to enter the probe through the other end of the probe, a sample support which supports the sample in a position where the sample is exposed to near field light emitted from the light outlet aperture of the probe, a diffusion panel which receives scattered light generated by interaction between the surface of the sample and the near field light and visualizes the intensity distribution pattern of the scattered light, an image taking means which takes an image of the intensity distribution pattern of the scattered light visualized by the diffusion panel, and a display means which displays the image of the intensity distribution pattern of the scattered light taken by the image taking means.

That is, in the sample analyzer, the intensity distribution pattern of the scattered light generated by interaction between the surface of the sample and the near field light is visualized and the image of the intensity distribution pattern is displayed.

The diffusion panel may double as the sample support.

The intensity distribution pattern of the scattered light is peculiar to a particular structure of the surface of a sample (e.g., orientation of molecules), and accordingly, the structure of the surface of the sample can be easily analyzed on the basis of correlations between the structures of the surfaces of the samples and the intensity distribution patterns of the scattered light peculiar to the respective structures which have been determined in advance.

In accordance with a second aspect of the present invention, there is provided a nano-aperture evaluation system for evaluating a light outlet aperture which is smaller in diameter than the wavelength of light comprising a light source for emitting evaluating light, an incident optical system which causes the evaluating light to enter the nano-aperture, a diffusion panel which receives light emanating from the nano-aperture and visualizes the intensity distribution pattern of the light, an image taking means which takes an image of the intensity distribution pattern of the light visualized by the diffusion panel, and a display means which displays the image of the intensity distribution pattern of the light taken by the image taking means.

That is, the nano-aperture evaluation system is for evaluating a nano-aperture in a probe employed in a near field optical microscope, a planar recording head using near field light and the like, and in the system, the intensity distribution pattern of part of light entering the nano-aperture which part emanates from the nano-aperture as propagating light is visualized by the diffusion panel and the image of the intensity distribution pattern is displayed.

It is preferred that the evaluation system be provided with a polarization control means which changes the state of polarization of light which enters the nano-aperture.

It has been known that there is a correlation between the intensity distribution pattern of propagating light emanating from a nano-aperture and that of near field light emanating from the nano-aperture. The correlation can be obtained by electromagnetic analysis such as the Bethe equation. Further since the intensity distribution pattern of near field light can be directly observed through a near field optical microscope, it is possible to relate the intensity distribution pattern of near field light observed through a near field optical microscope with that of propagating light in advance.

In accordance with the nano-aperture evaluation system, the intensity distribution pattern of near field light can be known on the basis of the intensity distribution pattern of the propagating light displayed by the display means and the correlation between the intensity distribution patterns of the near field light and the propagating light.

Further by changing the state of polarization of the light entering the light outlet nano-aperture and observing the intensity distribution pattern of the propagating light for each state of polarization, an optimal state of polarization of the light entering the aperture can be known.

Accordingly, evaluation of the nano-aperture of the aforesaid optical fiber probe can be carried out without use of a destructive inspection through an electron microscope.

Further the optimal state of polarization can be measured more easily at a higher yield as compared with the aforesaid method where another probe for measurement is caused to scan. Further since the intensity distribution pattern of the near field light is not affected by the probe for measurement, reliability of evaluation is improved.

DESCRIPTION OF THE PREFERRED EMBODIMENTS

Figure 1:
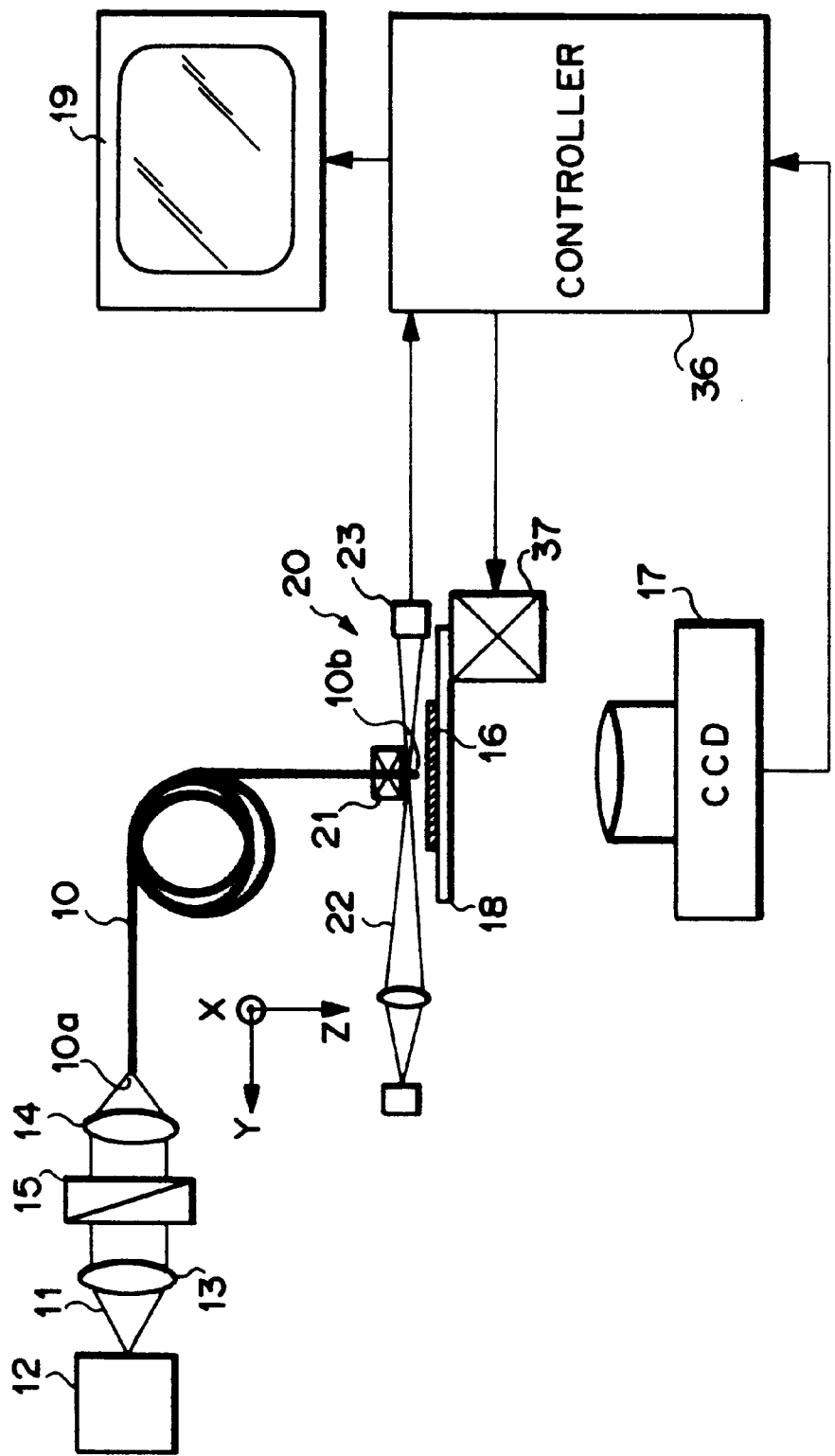
FIG. 1 is a side view of a sample analyzer in accordance with an embodiment of the present invention.

A sample analyzer in accordance with an embodiment of the present invention comprises a probe 10 having a light outlet nano-aperture at its free end 10b which is equivalent to that employed in a near field optical microscope, a laser 12 which emits a laser beam 11 for analyzing a sample, a collimator lens 13 which collimates the divergent laser beam 11, a condenser lens 14 which converges the collimated laser beam 11 on the base end (left end as seen in FIG. 1) 10a of the probe 10 and a λ/2 plate 15 which is disposed between the lenses 13 and 14 as a polarization control element.

The probe 10 is formed of, for instance, an optical fiber and the light outlet nano-aperture is formed at the free end 10b of the probe 10 which is sharpened. The laser beam 11 converged on the base end 10a of the probe 10 propagates through the probe 10 and emanates from the nano-aperture at the free end 10b of the probe 10.

At this time, evanescent light oozes out from the light outlet nano-aperture. When a sample 16 on a sample support 18 is exposed to the evanescent light, the evanescent light interacts with the sample 16 and generates scattered light which is propagating light. The sample support 18 is of a diffusion panel of either frosting or opal type and an image of the intensity distribution pattern of the scattered light is projected onto the diffusion panel and visualized. The projected image of the intensity distribution pattern is taken by a cooled CCD image taking device 17, and the image signal obtained is processed by a controller 36 and output to an image display means 19 such as a CRT.

The scattered light has an intensity distribution pattern peculiar to the shape and structure of the surface of the sample 16. Accordingly, by investigating the correlation between the intensity distribution pattern and the structure of the sample, more details of the structure of the sample such as orientations of molecules in the sample which cannot be determined by a near field optical microscope in which the intensity of the scattered light is detected in a fixed position can be analyzed.

Information on the two-dimensional shape and structure of the surface of the sample can be obtained by causing the probe 10 to two-dimensionally scan the surface of the sample and obtaining the intensity distribution pattern of the scattered light in each position of the surface of the sample.

In order to cause the probe 10 to scan the surface of the sample 16 with the probe 10 kept at a substantially constant distance from the surface of the sample 16, the sample support 18 is moved in X, Y and Z directions by a support drive means 37 which may comprise, for instance, a piezoelectric element.

The support drive means 37 is controlled by the controller 36. The position of the probe 10 in the optical axis is detected by a position sensor 20 and a position detecting signal output from the position sensor 20 is input into the controller 36. The controller 36 controls the support drive means 37 to set the sample support 18 (i.e., the sample 16) in a desired position in the Z direction on the basis of the position detecting signal. The detection and control of the position are carried out in the following manner. That is, the sample support 18 is moved up and down by the support drive means 37 to change the distance between the free end of the probe 10 and the surface of the sample 16 while resonating the free end portion of the probe 10 by a piezoelectric element 21 mounted on the free end portion of the probe 10. When the distance between the free end of the probe 10 and the surface of the sample 16 is reduced to a certain extent, van der Waals forces come to act and shearing force comes to act on the probe 10. The amplitude of vibration of the probe 10 changes with the shearing force. The amplitude of the vibration of the probe 10 is measured by converging a laser beam 22 on the free end of the probe 10 and detecting diffracted light by a photodetector 23. Since the amplitude of the vibration of the probe 10 depends on the distance between the free end 10b of the probe 10 and the surface of the sample 16, the free end 10b of the probe 10 can be set at a desired distance from the surface of the sample 16 by bringing the probe 10 by the support drive means 37 to a position where the amplitude of the vibration of the probe 10 becomes a value corresponding to the desired distance.

In this particular embodiment, by rotating the λ/2 plate 15 to change the orientation of the linear polarization of the laser beam 11 before entering the probe 10, the polarization can be set to a state optimal to analysis.

A nano-aperture evaluation system in accordance with an embodiment of the present invention will be described with reference to FIGS. 2 and 3, hereinbelow.

Figure 2:
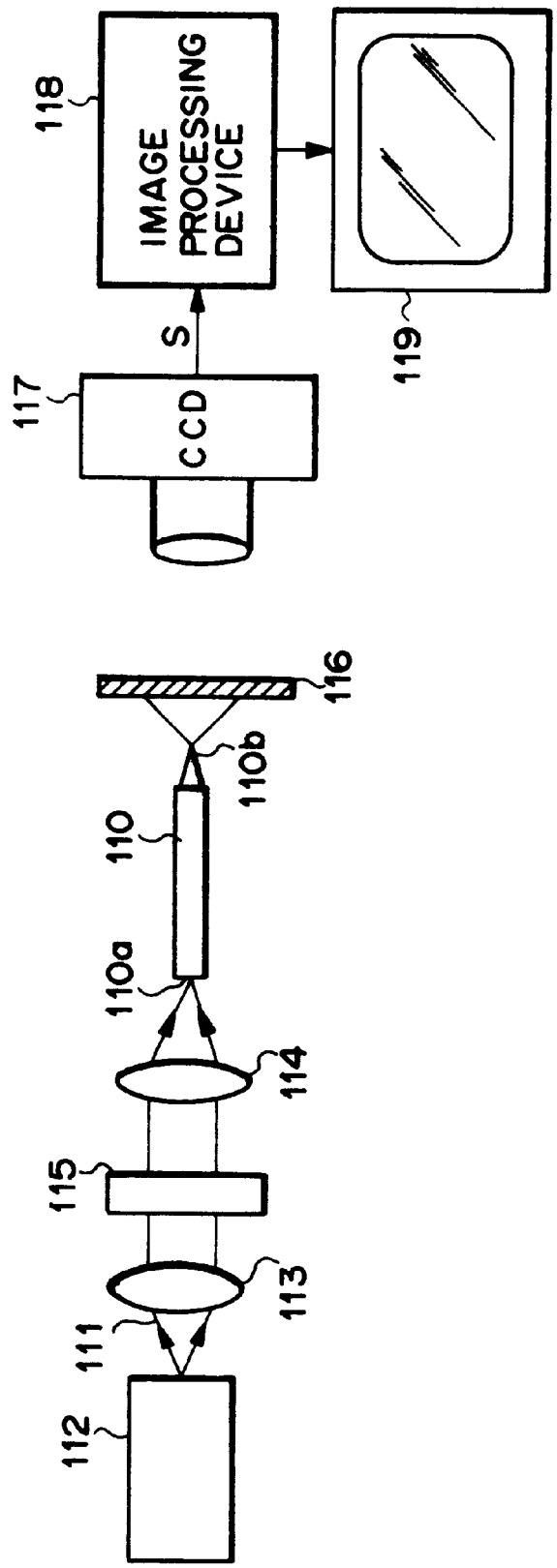
FIG. 2 is a view of a nano-aperture evaluation system in accordance with an embodiment of the present invention where the system is evaluating the performance of a probe with a nano-aperture for use in a near field optical microscope or the like, and FIG. 3 is a view of the nano-aperture evaluation system where the system is evaluating a planar device having a plurality of nano-apertures.

The nano-aperture evaluation system of this embodiment is for evaluating the performance of a probe 110 with a nano-aperture for use, for instance, in a near field optical microscope and comprises a laser 112 which emits a laser beam 111 for evaluation, a collimator lens 113 which collimates the divergent laser beam 111, a condenser lens 114 which converges the collimated laser beam 111 on the base end (left end as seen in FIG. 2) 110a of the probe 110 and a λ/2 plate 115 which is disposed between the lenses 113 and 114 as a polarization control element.

The probe 110 is formed of, for instance, an optical fiber and has a flat base end 110a and a sharpened free end 10b. A light outlet nano-aperture smaller in diameter than the wavelength of light is formed at the free end 110b of the probe 110. The laser beam 111 converged on the base end 110a of the probe 110 propagates through the probe 110 and emanates from the nano-aperture at the free end 110b of the probe 110 in a divergent state.

At this time, evanescent light emanates from the light outlet nano-aperture together with the laser beam 111 which is ordinary propagating light. Though, in a near field optical microscope or the like, the evanescent light is used for observation, analysis, processing or the like of a sample, it is not directly used in evaluation of the probe 110.

The laser beam 111 emanating from the nano-aperture on the free end 110b of the probe 110 in a divergent state impinges upon a diffusion panel 116. An image of the intensity distribution pattern of the laser beam 111 projected onto the diffusion panel 116 is taken by a cooled CCD image taking device 117 disposed behind the diffusion panel 116. An image signal output from the CCD image taking device 117 is processed by an image processing device 118 and input into an image display means 119 such as a CRT.

When evaluating the probe 110, the laser beam 111 is caused to enter the probe 110 and the laser beam (propagating light) 111 emanating from the nano-aperture is projected onto the diffusion plate 116. The projected image of the laser beam 111 is taken by the cooled CCD image taking element 117. The projected image represents the intensity distribution pattern in a cross-section of the laser beam 111. An image signal representing the intensity distribution pattern is input into the image processing device 118 and is subjected to a predetermined image processing. Then the processed image signal is input into the image display means 119. Thus an image of the intensity distribution pattern of the propagating light 111 emanating from the probe 110 is displayed by the image display means 119.

As described above, there is a correlation between the intensity distribution pattern of propagating light emanating from the nano-aperture of the probe 110 and that of near field light emanating from the nano-aperture of the probe 110. Accordingly, the intensity distribution pattern of the near field light can be known from the intensity distribution pattern of the laser beam 111 displayed by the image display means 119 on the basis of the correlation therebetween, whereby the performance of the nano-aperture or the probe can be evaluated.

In this embodiment, by rotating the λ/2 plate 115 to change the orientation of the linear polarization of the laser beam 111 before entering the probe 110, the intensity distribution pattern of the laser beam 111 for each state of polarization can be observed, whereby the state of polarization where the intensity distribution pattern of propagating light (accordingly of near field light) becomes optimal can be known.

The nano-aperture evaluation system of this embodiment can also be used for evaluating a planar device such as a recording head comprising a planar substrate provided with a plurality of nano-apertures as shown in FIG. 3. As shown in FIG. 3, while moving the planar device 120 as shown by the arrow, the intensity distribution pattern of the laser beam 111 emanating from each nano-aperture is projected onto the diffusion panel 116 and the image of the intensity distribution pattern is displayed by the image display means 119.

What is claimed is:

1. A sample analyzer comprising:

a light source for emitting light for analyzing the sample, a probe having at its one end a light outlet aperture which is smaller in diameter than a wavelength of the light emitted from the light source, an incident optical system which causes the light emitted from the light source to enter the probe through the other end of the probe, a sample support which supports a sample in a position where the sample is exposed to near field light emitted from the light outlet aperture of the probe, a diffusion panel which receives scattered light generated by interaction between a surface of the sample and the near field light and visualizes an intensity distribution pattern of the scattered light, an image taking means which takes an image of the intensity distribution pattern of the scattered light visualized by the diffusion panel, and a display means which displays the image of the intensity distribution pattern of the scattered light taken by the image taking means.

2. A sample analyzer as defined in claim 1, in which the diffusion panel doubles as the sample support.

3. A nano-aperture evaluation system for evaluating a light outlet aperture which is smaller in diameter than a wavelength of light comprising a light source for emitting evaluating light, an incident optical system which causes the evaluating light to enter a nano-aperture, a diffusion panel which receives light emanating from the nano-aperture and visualizes an intensity distribution pattern of the light, an image taking means which takes an image of the intensity distribution pattern of the light visualized by the diffusion panel, and a display means which displays the image of the intensity distribution pattern of the light taken by the image taking means.

4. A nano-aperture evaluation system as defined in claim 3, further comprising a polarization control means which changes a state of polarization of light which enters the nano-aperture.

* * * * *